(12) United States Patent
Kang et al.

(10) Patent No.: US 11,877,858 B2
(45) Date of Patent: Jan. 23, 2024

(54) APPARATUS AND METHOD FOR ESTIMATING BIO-INFORMATION

(71) Applicant: SAMSUNG ELECTRONICS CO., LTD., Suwon-si (KR)

(72) Inventors: Jae Min Kang, Seoul (KR); Seung Woo Noh, Seongnam-si (KR); Sang Yun Park, Hwaseong-si (KR); Jin Woo Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 637 days.

(21) Appl. No.: 16/950,140

(22) Filed: Nov. 17, 2020

(65) Prior Publication Data

US 2021/0401357 A1 Dec. 30, 2021

(30) Foreign Application Priority Data

Jun. 30, 2020 (KR) ........................ 10-2020-0080145

(51) Int. Cl.
*A61B 5/00* (2006.01)
*A61B 5/1455* (2006.01)
(Continued)

(52) U.S. Cl.
CPC .......... *A61B 5/442* (2013.01); *A61B 5/02007* (2013.01); *A61B 5/02116* (2013.01); *A61B 5/743* (2013.01); *G06F 3/04146* (2019.05); *G06F 18/22* (2023.01); *G06V 40/1318* (2022.01); *G06V 40/1353* (2022.01); *G06V 40/67* (2022.01); *G06F 2203/04105* (2013.01); *G06V 40/14* (2022.01)

(58) Field of Classification Search
CPC . A61B 5/442; A61B 5/02004; A61B 5/02116; A61B 5/743; A61B 5/02416; A61B 5/1172; A61B 5/0205; A61B 5/441; G06V 40/1318; G06V 40/1353; G06V 40/1359; G06F 2203/04106
See application file for complete search history.

(56) References Cited

U.S. PATENT DOCUMENTS

2008/0162352 A1 7/2008 Gizewski
2012/0305646 A1 12/2012 Schweikart et al.
(Continued)

FOREIGN PATENT DOCUMENTS

KR 20-0355325 Y1 7/2004
KR 10-0660349 B1 12/2006
(Continued)

OTHER PUBLICATIONS

Communication dated Oct. 15, 2021, issued by the European Patent Office in counterpart European Application No. 21179774.1.

*Primary Examiner* — Chu Chuan Liu
(74) *Attorney, Agent, or Firm* — Sughrue Mion, PLLC

(57) ABSTRACT

An apparatus for estimating bio-information according to an embodiment of the present disclosure includes a first sensor configured to obtain a fingerprint image of a finger of the user; a second sensor configured to measure a force or a pressure applied by the finger; and a processor configured to obtain, based on the fingerprint image, a first feature value related to pulse waves and a second feature value related to skin elasticity; obtain a third feature value based on the force or the pressure; and estimate the bio-information of the user based on the first feature value, the second feature value, and the third feature value.

29 Claims, 16 Drawing Sheets

(51) Int. Cl.
  *G06F 3/041*  (2006.01)
  *G06V 40/60*  (2022.01)
  *G06V 40/12*  (2022.01)
  *A61B 5/02*   (2006.01)
  *A61B 5/021*  (2006.01)
  *G06V 40/13*  (2022.01)
  *G06F 18/22*  (2023.01)
  *G06V 40/14*  (2022.01)

(56) References Cited

U.S. PATENT DOCUMENTS

| | | |
|---|---|---|
| 2014/0276031 A1 | 9/2014 | Lomnitz et al. |
| 2014/0359757 A1* | 12/2014 | Sezan .................... G06F 21/32 |
| | | 726/19 |
| 2017/0095168 A1* | 4/2017 | Kwon .................. A61B 5/1172 |
| 2017/0337412 A1* | 11/2017 | Bhat .................... A61B 5/1172 |
| 2018/0014777 A1 | 1/2018 | Amir et al. |
| 2018/0276440 A1* | 9/2018 | Strohmann ........ G06V 40/1359 |
| 2018/0276443 A1 | 9/2018 | Strohmann et al. |
| 2020/0019745 A1 | 1/2020 | Kang et al. |
| 2020/0037956 A1 | 2/2020 | Kang et al. |
| 2020/0077904 A1 | 3/2020 | Kang et al. |

FOREIGN PATENT DOCUMENTS

| | | |
|---|---|---|
| KR | 10-2011-0022898 A | 3/2011 |
| KR | 10-1380451 B1 | 4/2014 |
| KR | 10-2015-0143063 A | 12/2015 |
| KR | 10-2018-0016885 A | 2/2018 |

* cited by examiner

APPARATUS AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2020-0080145, filed on Jun. 30, 2020, in the Korean Intellectual Property Office, the disclosure of which is incorporated by reference herein in its entirety.

BACKGROUND

1. Field

The following description relates to an apparatus and method for estimating bio-information, and technology for cuffless blood pressure estimation.

2. Description of Related Art

Generally, methods of non-invasively measuring blood pressure without damaging a human body include a method to measure blood pressure by measuring a cuff-based pressure and a method to estimate blood pressure by measuring pulse waves without the use of a cuff.

A Korotkoff-sound method is one of the cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large.

Cuffless blood pressure measurement methods generally include a method of estimating blood pressure by calculating a Pulse Transit Time (PTT), and a Pulse Wave Analysis (PWA) method of estimating blood pressure by analyzing a pulse wave shape.

SUMMARY

According to an aspect of an example embodiment, an apparatus for estimating bio-information of a user may include a first sensor configured to obtain a fingerprint image of a finger of the user; a second sensor configured to measure a force or a pressure applied by the finger; and a processor configured to obtain, based on the fingerprint image, a first feature value related to pulse waves and a second feature value related to skin elasticity; obtain a third feature value based on the force or the pressure; and estimate the bio-information of the user based on the first feature value, the second feature value, and the third feature value.

The first sensor may include one or more light sources configured to emit light onto the finger; and one or more complementary metal-oxide semiconductor (CMOS) image sensors.

The processor may obtain a pulse wave signal based on the fingerprint image; and obtain the first feature value based on at least one of a maximum amplitude value and a minimum amplitude value of the pulse wave signal.

The processor may obtain a change in distance between ridges or valleys of a fingerprint from the fingerprint image based on the finger pressing the first sensor; and obtain the second feature value based on the change in distance.

The processor may obtain a first average of distances between the ridges or the valleys at one or more points of first fingerprint images obtained continuously over a predetermined period of time, and a second average of the distances at one or more points of a second fingerprint image; and obtain a difference between the first average and the second average as the change in distance.

The processor may generate a graph of a fingerprint pattern change based on the change in distance; and obtain the second feature value based on the graph of the fingerprint pattern change.

The processor may obtain, as the second feature value, at least one of a maximum slope value, a minimum slope value, and an average slope value of each of pre-defined unit intervals.

The processor may generate a differential graph by differentiating the graph of the fingerprint pattern change; and obtain the second feature value by using the differential graph.

The processor may obtain a force value or a pressure value at a point in time, corresponding to the first feature value, as the third feature value.

The processor may combine the first feature value, the second feature value, and third feature value; and estimate the bio-information by applying a pre-defined estimation model to a result of combining the first feature value, the second feature value, and the third feature value.

The processor may apply a first weight to the first feature value to obtain a first weighted value; apply a second weight to the second feature value to obtain a second weighted value; apply a third weight to the third feature value to obtain a third weighted value; and combine the first weighted value, the second weighted value, and the third weighted value.

Each of the first weight value, the second weight value, and the third weight value may be a pre-defined fixed value, or a value adjusted by considering at least either user characteristics or types of bio-information.

The processor may, while the fingerprint image is obtained from the finger, control an output interface to output guide information to guide a user regarding pressure between the finger and the first sensor.

The bio-information may include one or more of blood pressure, vascular age, arterial stiffness, aortic pressure waveform, vascular compliance, stress index, and fatigue level.

A method of estimating bio-information of a user may include obtaining a fingerprint image of a finger of the user; measuring a force or a pressure applied by the finger; obtaining a first feature value related to pulse waves based on the fingerprint image; obtaining a second feature value related to skin elasticity based on the fingerprint image; obtaining a third feature value based on the force or the pressure; and estimating the bio-information based on the first feature value, the second feature value, and the third feature value.

The obtaining of the first feature value may include obtaining a pulse wave signal from the fingerprint image; and obtaining the first feature value based on at least one of a maximum amplitude value and a minimum amplitude value of the pulse wave signal.

The obtaining of the second feature value may include obtaining a change in distance between ridges or valleys of a fingerprint from the fingerprint image based on the finger pressing the first sensor; and obtaining the second feature value based on the obtained change in distance.

The obtaining of the second feature value may include obtaining a first average of first distances between the ridges or the valleys at one or more points of first fingerprint images obtained continuously over a predetermined period of time; obtaining a second average of second distances between the ridges or the valleys at one or more points of a second fingerprint image; and obtaining a difference between the first average and the second average as the change in distance.

The obtaining of the second feature value may include generating a graph of a fingerprint pattern change based on the change in distance; and obtaining the second feature value based on the graph of the fingerprint pattern change.

The obtaining of the second feature value may include obtaining, as the second feature value, at least one of a maximum slope value, a minimum slope value, and an average slope value of each of pre-defined unit intervals.

The obtaining of the third feature value may include obtaining a force value or a pressure value at a point in time, corresponding to the first feature value, as the third feature value.

The estimating of the bio-information may include combining the first feature value, the second feature value, and the third feature value; and estimating the bio-information by applying a pre-defined estimation model to a result of combining the first feature value, the second feature value, and the third feature value.

The method may include, while the fingerprint image is being obtained from the finger, guiding a user regarding pressure between the finger and a sensor.

According to an aspect of an example embodiment, an apparatus for estimating bio-information of a user may include a first sensor configured to obtain a fingerprint image of a finger of the user; a second sensor configured to measure a force or a pressure applied by the finger; and a processor configured to obtain two or more feature values based on at least one of the fingerprint image and the force or the pressure; and estimate first bio-information and second bio-information, based on the two or more feature values.

The first bio-information may be blood pressure; and the processor may obtain a first feature value and a second feature value based on the fingerprint image; obtain a third feature value based on the first feature value and the force or the pressure; and estimate the blood pressure by combining the first feature value and the second feature value.

The second bio-information may be at least one of skin elasticity and skin age; and the processor may obtain the second feature value based on the fingerprint image; and estimate at least one of the skin elasticity and the skin age based on the second feature value.

The processor may obtain a change in distance between ridges or valleys of the fingerprint from the fingerprint image based on the finger pressing the first sensor; and obtain the second feature value based on the change in distance.

The processor may estimate that the skin elasticity decreases or increases, and that the skin age increases or decreases as a change in the second feature value shows an increasing or decreasing trend, compared to a second feature value obtained at a reference time.

According to an aspect of an example embodiment, an apparatus for estimating bio-information of a user may include a sensor configured to obtain a fingerprint image of a finger of the user based on the finger pressing the sensor; and a processor configured to obtain feature values from the fingerprint image based on a fingerprint pattern change based on the finger pressing the sensor; and estimate at least one of skin elasticity and skin age based on the feature values.

The sensor may measure a force or a pressure applied by the finger; and the processor may obtain a change in distance between ridges or valleys of the fingerprint from the fingerprint image based on the finger pressing the sensor; generate a graph of a fingerprint pattern change by plotting the change in distance against the force or the pressure; and obtain the feature values by using the graph of the fingerprint pattern change.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
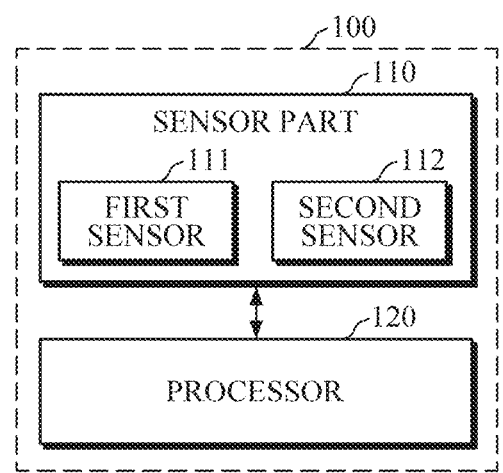
FIGS. 1 and 2 are block diagrams illustrating examples of an apparatus for estimating bio-information.

Details of example embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms "first," "second," etc. may be used herein to describe various elements, these elements should not be limited by these terms. These terms are used to distinguish one element from another. Also, the singular forms of terms are intended to include the plural forms of the terms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation, and the unit may be implemented by using hardware, software, or a combination thereof.

Hereinafter, embodiments of an apparatus and method for estimating bio-information will be described in detail with reference to the accompanying drawings.

Figure 2:
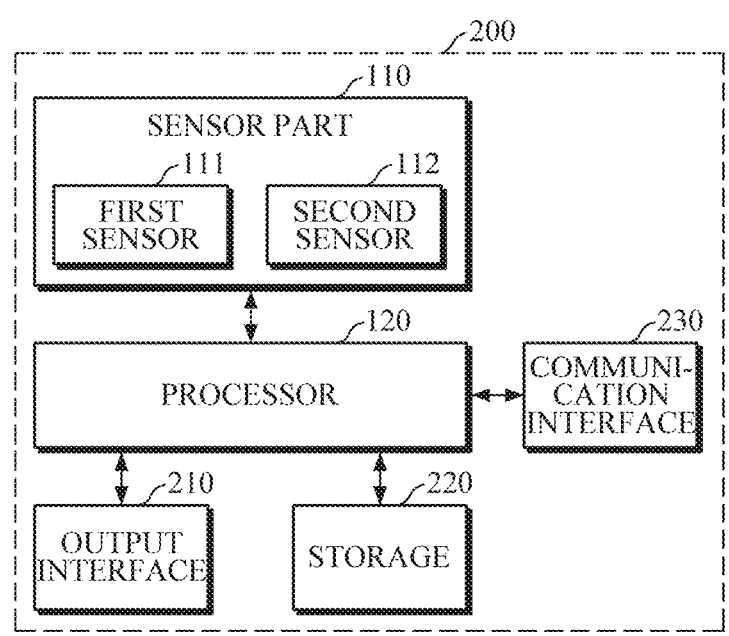

FIGS. 1 and 2 are block diagrams illustrating examples of an apparatus for estimating bio-information.

The apparatuses 100 and 200 for estimating bio-information according to the embodiments of the present disclosure may be mounted in medical devices used in specialized medical institutions, a smartwatch worn on a wrist, various types of wearable devices such as a smart band type wearable device, a headphone type wearable device, a headband type wearable device, etc., or a mobile device such as a smartphone, a tablet personal computer (PC), etc., but are not limited thereto.

Referring to FIGS. 1 and 2, the apparatuses 100 and 200 for estimating bio-information include a sensor part 110 and a processor 120.

The sensor part 110 may include a first sensor 111 for obtaining a fingerprint image when a finger touches the sensor part 110, and a second sensor 112 for measuring force or pressure when the finger touches and presses the first sensor 111.

The first sensor 111 may include one or more light sources for emitting light onto the finger, and one or more detectors for detecting light scattered or reflected from the finger. The light source may include a light emitting diode (LED), a laser diode (LD), a phosphor, and the like, but is not limited thereto. The detector may include a complementary metal-oxide semiconductor (CMOS) image sensor (CIS). However, the detector is not limited thereto, and may include a charge-coupled device (CCD) image sensor, a photodiode, a photo transistor, and the like. The plurality of light sources may emit light of the same wavelength or light of different wavelengths. The plurality of detectors may be positioned at different distances from the light sources.

The second sensor 112 may include a force sensor, an array of force sensors, a pressure sensor, an air bladder type pressure sensor, a pressure sensor including a combination of force and area sensors, and the like.

For example, the first sensor 111 may include a finger contact surface, on which the finger is placed. The finger contact surface may be formed as a smooth curved surface, but is not limited thereto. In this case, the second sensor 112 may be disposed on a lower end of the first sensor 111, so that when the finger is placed on the finger contact surface of the first sensor 111 and gradually increases or decreases a pressing force or pressure, the second sensor 112 may measure the pressing force or pressure.

In another example, in the case where the second sensor 112 is a pressure sensor including a combination of force and area sensors, the area sensor, the first sensor 111, and the force sensor are arranged in a stacked structure, and the finger contact surface may be formed on the area sensor. When the finger is in contact with the finger contact surface of the area sensor and changes a pressing force, the area sensor may obtain a contact area of the finger and the force sensor may measure the pressing force.

The processor 120 may be electrically connected to the sensor part 110. The processor 120 may control the sensor part 110 in response to a user's request, and may receive data from the sensor part 110. Further, the processor 120 may estimate bio-information by using the data received from the sensor part 110.

For example, the processor 120 may obtain one or more feature values based on the fingerprint image of the finger, which is obtained by the first sensor 111, and the force or pressure measured by the second sensor 112, and may estimate bio-information by using the obtained feature values. In this case, the bio-information may include, but is not limited to, heart rate, blood pressure, vascular age, arterial stiffness, aortic pressure waveform, vascular compliance, stress index, fatigue level, skin elasticity, skin age, and the like. For convenience of explanation, the following description will be given using blood pressure, skin elasticity, and skin age as examples.

For example, the processor 120 may obtain a pulse wave signal from the fingerprint image of the finger, and may obtain a first feature value, related to pulse waves, by using the obtained pulse wave signal. In addition, the processor 120 may obtain a second feature value, related to skin elasticity, from the fingerprint image of the finger, and may obtain a third feature value based on the force or pressure of the finger. Furthermore, the processor 120 may combine two or more of the first, second, and third feature values, and may estimate blood pressure by applying a pre-defined blood pressure estimation model to the combined value. Alternatively, the processor 120 may estimate the skin elasticity and/or skin age by using the second feature value.

Referring to FIG. 2, the apparatus 200 for estimating bio-information according to another embodiment of the present disclosure may further include an output interface 210, a storage 220, and a communication interface 230, in addition to the sensor part 110 and the processor 120. The sensor part 110 and the processor 120 are described above, such that the following description will be focused on the output interface 210, the storage 220, and the communication interface 230.

Based on receiving a request for estimating bio-information, the processor 120 may obtain a reference pressure by referring to the storage 220, and may generate guide information for guiding a user to maintain pressure of the user's finger, pressing the sensor part 110, within a reference pressure range. Further, based on the sensor part 110 measuring the force and pressure, the processor 120 may generate guide information for guiding an actual force or pressure applied by the finger to the sensor part 110. In this case, the guide information may include information for guiding an object to gradually increase pressure when the object touches and presses the sensor part 110, or by contrast, information for guiding the object to gradually decrease pressure when the object initially applies contact pressure greater than or equal to a predetermined threshold value to the sensor part 110.

The output interface 210 may output the fingerprint image and/or the force/pressure, obtained by the sensor part 110, and an estimated bio-information value and/or guide information obtained by the processor 120. For example, the output interface 210 may visually output data, processed by the sensor part 110 or the processor 120, through a display module, or may non-visually output the information by voice, vibrations, tactile sensation, and the like, using a speaker module, a haptic module, and the like. In this case, a display area may be divided into two or more areas, in which the output interface 210 may output the fingerprint image, the pulse wave signal, the force or pressure, etc., which are used for estimating bio-information, in the form of various graphs in a first area; and along with the information, the output interface 210 may output an estimated bio-information value in a second area. In this case, if the estimated bio-information value falls outside a normal range, the output interface 210 may output warning information in various manners, such as highlighting an abnormal value in red, and the like, displaying the abnormal value along with a normal range, outputting a voice warning message, adjusting a vibration intensity, and the like.

The storage 220 may store results processed by the sensor part 110 and the processor 130. Further, the storage 220 may store a variety of reference information for estimating bio-information. For example, the reference information may include user characteristic information such as a user's age, gender, health condition, and the like. In addition, the reference information may include a bio-information estimation model, criteria for estimating bio-information, reference pressure, etc., but is not limited thereto.

In this case, the storage 220 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 230 may communicate with an external device by using wired or wireless communication techniques under the control of the processor 120, and may transmit and receive various data to and from the external device. For example, the communication interface 230 may transmit a bio-information estimation result to the external device, and may receive a variety of reference information for estimating bio-information from the external device. In this case, the external device may include a cuff-type blood pressure measuring device and an information processing device such as a smartphone, a tablet PC, a desktop computer, a laptop computer, and the like.

In this case, examples of the communication techniques may include Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, 3G communication, 4G communication, 5G communication, and the like. However, this is merely exemplary and is not intended to be limiting.

Figure 3A:
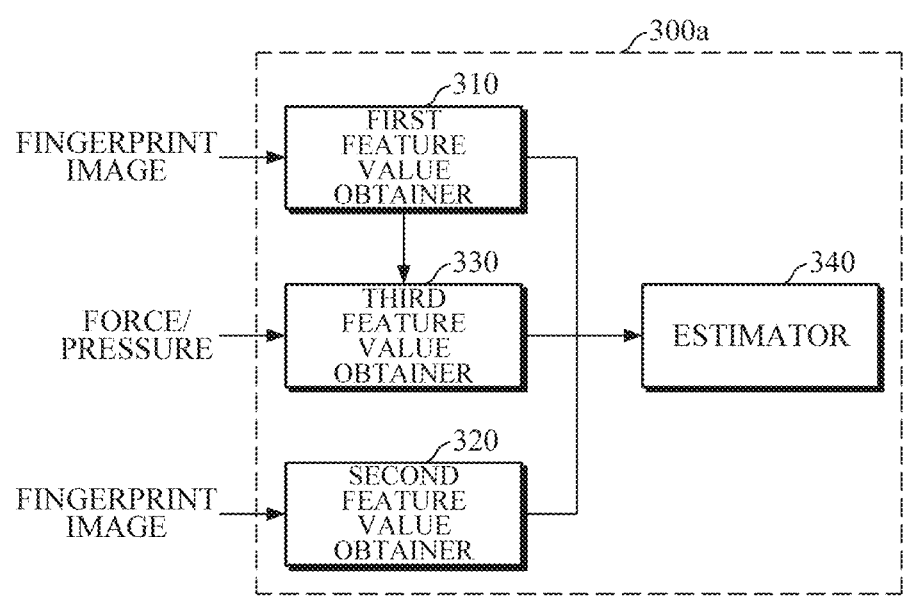
FIGS. 3A and 3B are diagrams illustrating examples of a configuration of a processor of an apparatus for estimating bio-information.

FIG. 3A is a diagram illustrating an example of a configuration of a processor of an apparatus for estimating bio-information. FIGS. 4A to 6C are diagrams explaining examples of obtaining feature values.

Referring to FIG. 3A, a processor 300a according to an embodiment of the present disclosure includes a first feature value obtainer 310, a second feature value obtainer 320, a third feature value obtainer 330, and an estimator 340.

Based on receiving a fingerprint image from the first sensor 111, the first feature value obtainer 310 may obtain a pulse wave signal based on the fingerprint image. For example, the first feature value obtainer 310 may obtain the pulse wave signal based on a change in intensity of fingerprint images which are obtained continuously over a predetermined period of time. When a pressing force or pressure of the finger on the sensor part 110 gradually increases or decreases, amplitude values of the pulse wave signal, obtained from the fingerprint image, have a gradually increasing or decreasing pattern. By analyzing an increasing or decreasing waveform of the pulse wave signal, the first feature value obtainer 310 may obtain the first feature value.

In this case, the first feature value may include a maximum amplitude value and/or a minimum amplitude value of the pulse wave signal. However, the first feature value is not limited thereto, and may include amplitude values at points related to propagation and reflection waves, a partial area of a waveform of the pulse wave signal, and the like.

The second feature value obtainer 320 may obtain a second feature value, related to skin elasticity, based on the fingerprint image received from the first sensor 111. When a user touches the sensor part 110 with a finger and increases or decreases a pressing force or pressure of the finger on the sensor part 110, a change in fingerprint pattern of the finger is shown in the fingerprint image according to skin elasticity. Accordingly, based on the change in fingerprint pattern shown in the fingerprint image, the second feature value obtainer 320 may obtain the second feature value related to skin elasticity.

For example, the second feature value obtainer 320 may obtain a change in distance between ridges or valleys of the fingerprint or a pressed degree of the fingerprint pattern, and may obtain the second feature value, related to skin elasticity, based on the obtained change in distance between ridges or valleys or the obtained pressed degree of the fingerprint pattern. In this case, in order to reflect characteristics that the pressed degree of the fingerprint pattern varies according to positions of the fingerprint, the second feature value obtainer 320 may obtain distances between the ridges or valleys at two or more points of the fingerprint image, and may obtain the second feature value based on a change in statistical value, such as an average of the obtained distances.

The third feature value obtainer 330 may obtain a third feature value based on the force or pressure received from the second sensor 112. For example, the third feature value obtainer 330 may obtain, as the third feature value, a force or pressure value at a point in time when the first feature value is obtained by the first feature value obtainer 310. However, the third feature value is not limited thereto.

FIGS. 4A to 6C are diagrams explaining examples of obtaining feature values.

Figure 4A:
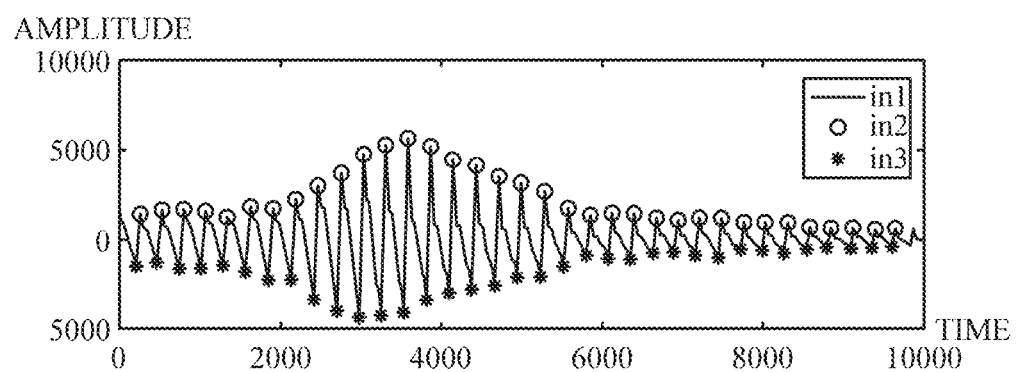
FIGS. 4A to 6C are diagrams explaining examples of obtaining feature values.

FIG. 4A is a diagram illustrating an example of a pulse wave signal obtained based on a change in intensity of fingerprint images which are obtained continuously when a user touches the sensor part 110 with a finger for a predetermined period of time and gradually increases a pressing force of the finger. By using the obtained pulse wave signal, the first feature value obtainer 310 may obtain, for example, a maximum amplitude value of the pulse wave signal as the first feature value.

Figure 4B:
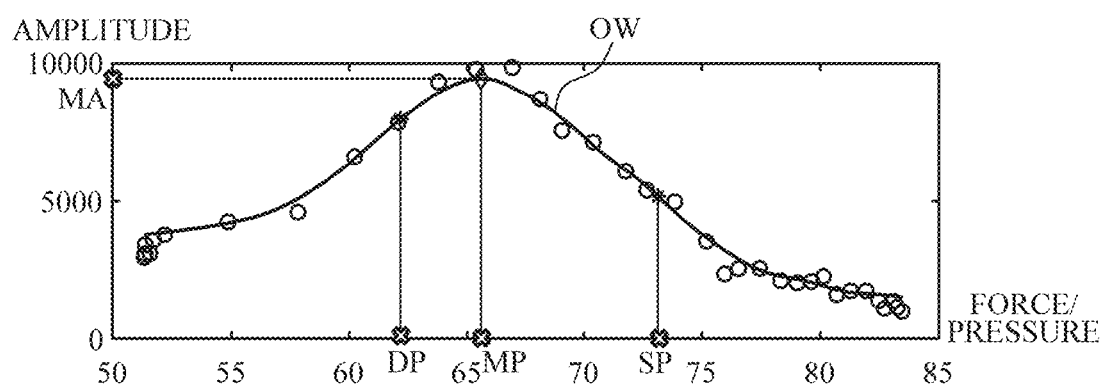

FIG. 4B is a diagram explaining examples of the third feature value obtained by the third feature value obtainer 330, and illustrating an oscillometric waveform (OW) graph showing a relationship between a change in amplitude of the pulse wave signal during a predetermined period of time and a change in force or pressure measured by the second sensor. The third feature value obtainer 330 may extract a peak-to-peak point of the pulse wave signal waveform by subtracting a negative (−) amplitude value in3 from a positive (+) amplitude value in2 of a waveform envelope in1 at each measurement time of the pulse wave signal, and may obtain the oscillometric waveform envelope (OW) by plotting the peak-to-peak amplitude at each measurement time against the force/pressure value at the same point in time.

Based on the first feature value obtainer 310 obtaining, for example, a maximum amplitude value MA as the first feature value, the third feature value obtainer 330 may obtain, as the third feature value, a force/pressure value MP at a point in time corresponding to the maximum amplitude value MA. However, the third feature value is not limited thereto, and the third feature value obtainer 330 may also obtain force/pressure values DP and SP at the left and right points in time, corresponding to amplitude values having a preset ratio (e.g., 0.5 to 0.7) to the maximum amplitude value MA, etc., as additional third feature values.

Figure 5A:
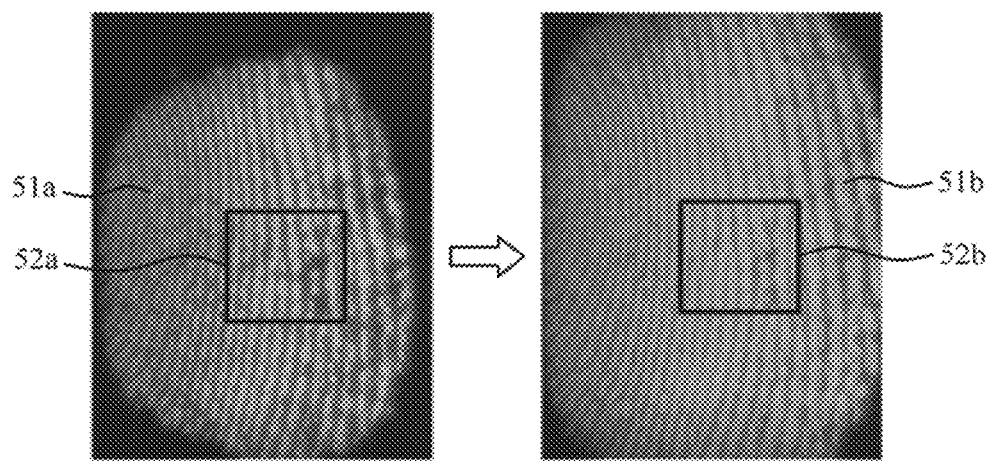
Figure 5B:
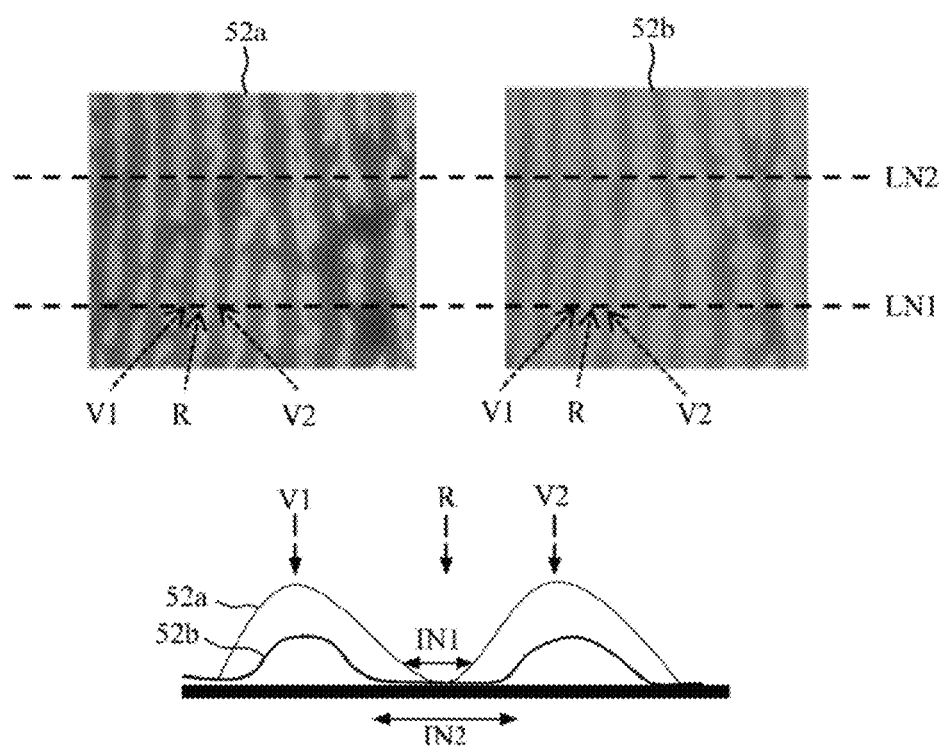
Figure 5C:
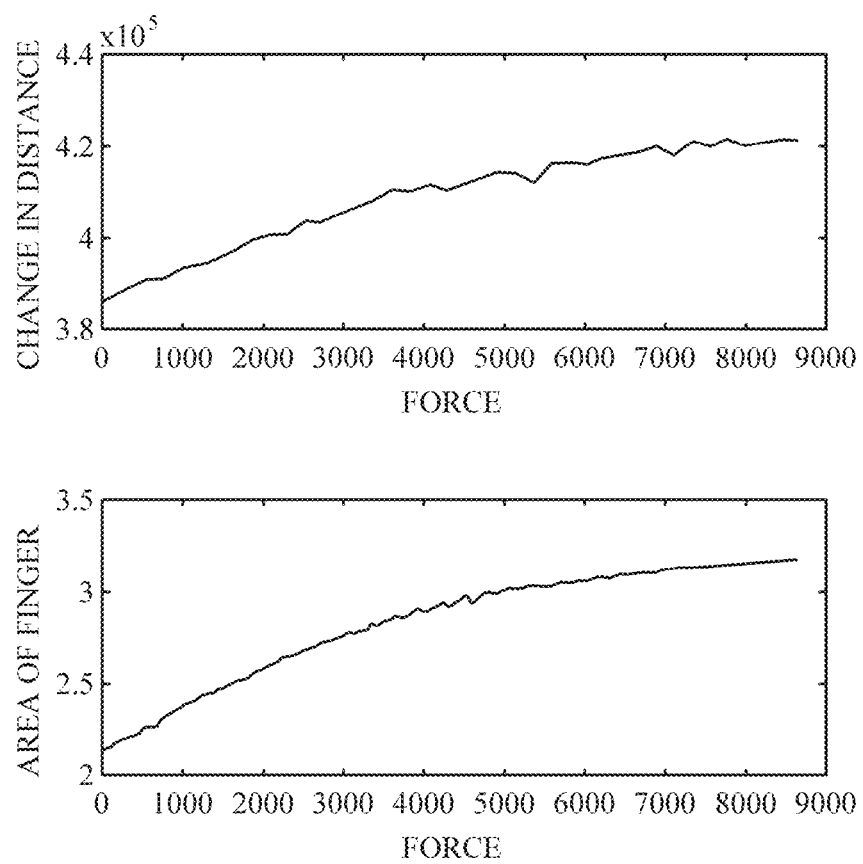

FIGS. 5A to 5C are diagrams explaining an example in which the second feature value obtainer 320 obtains the second feature value from the fingerprint image.

Referring to FIG. 5A, there is a change in fingerprint pattern between a first fingerprint image 51a measured at a first time and a second fingerprint image 51b measured at a second time, among fingerprint images measured continuously over a predetermined period of time. That is, as measurement proceeds from the first time to the second time, if a force applied by the finger to the sensor part 110 gradually increases, the finger is pressed gradually such that a distance between ridges or valleys of the fingerprint is changed as illustrated in FIG. 5A.

FIG. 5B is a diagram explaining a change in distance between ridges or valleys of a fingerprint, and illustrating an enlarged view of a first fingerprint area 52a in the first fingerprint image M a and a second fingerprint area 52b corresponding to the first fingerprint area 52a in the second fingerprint image Mb. As illustrated in FIG. 5B, at the first time when a weak force is applied by the finger, a pressed degree of the fingerprint is relatively low, such that a height of a first valley V1 and a second valley V2 is high and a distance IN1 of a ridge R between the first valley V1 and the second valley V2 is relatively small in the first fingerprint area 52a. By contrast, at the second time when a relatively strong force is applied by the finger, a pressed degree of the fingerprint is relatively high, such that a height of the first valley V1 and the second valley V2 is relatively low and a distance IN2 of a ridge R between the first valley V1 and the second valley V2 is relatively large in the second fingerprint area 52b.

As described above, by using the fingerprint images obtained continuously over a predetermined period of time, the second feature value obtainer 320 may obtain a change in a ridge distance between valleys or a change in a valley distance between ridges. In this case, in order to reflect characteristics of the fingerprint at a plurality of positions of the finger, the second feature value obtainer 320 may obtain, as the change in the ridge or valley distance, a change between an average of distances at two or more points LN1 and LN2 of the first fingerprint image Ma and an average of distances between two or more corresponding points LN1 and LN2 of the second fingerprint image Mb.

FIG. 5C illustrates, in an upper view, a graph of a fingerprint pattern change showing a relationship between a change in pressing force of the finger on the sensor part 110 and a change in distance between valleys or ridges which is obtained based on fingerprint images; and in a lower view, a graph showing a relationship between a change in pressing force of the finger and a change in an actual area of the finger which is obtained by an area sensor. As illustrated in FIG. 5C, when a user gradually increases a pressing force of the finger, the area of the finger increases nonlinearly for a predetermined period of time and is saturated. The trend of the change in area of the finger varies depending on individual characteristics such as a user's gender, age, skin elasticity of the finger, and the like. As shown in FIG. 5C, the change in distance vs. force of the finger shows a similar trend to the change in area of the finger, such that based on the change in distance between valleys or ridges, the second feature value obtainer 320 may obtain the second feature value related to the skin elasticity of the finger.

Figure 6A:
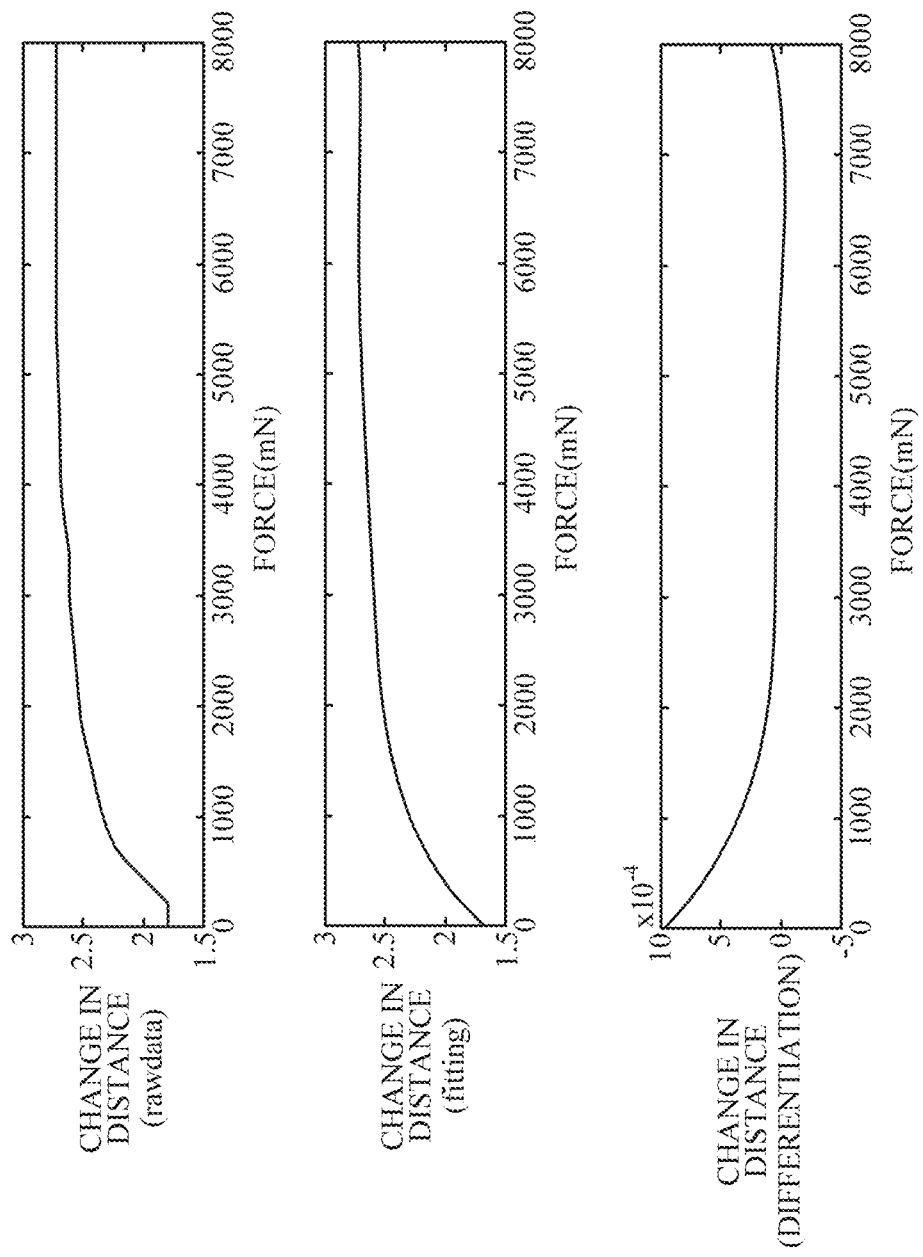

Referring to FIG. 6A, by plotting the change in distance between valleys or ridges against a pressing force/pressure of the finger at each time point on a time axis, the second feature value obtainer 320 may generate a graph (upper view) of a fingerprint pattern change, which shows the change in distance vs. force/pressure. Further, the second feature value obtainer 320 may perform a multi-dimensional equation curve fitting (middle view) on the fingerprint pattern change graph (upper view), and may generate a differential graph (lower view) by performing differentiation based on the force/pressure. By using the generated differential graph (lower view), the second feature value obtainer 320 may obtain the second feature value.

Figure 6B:
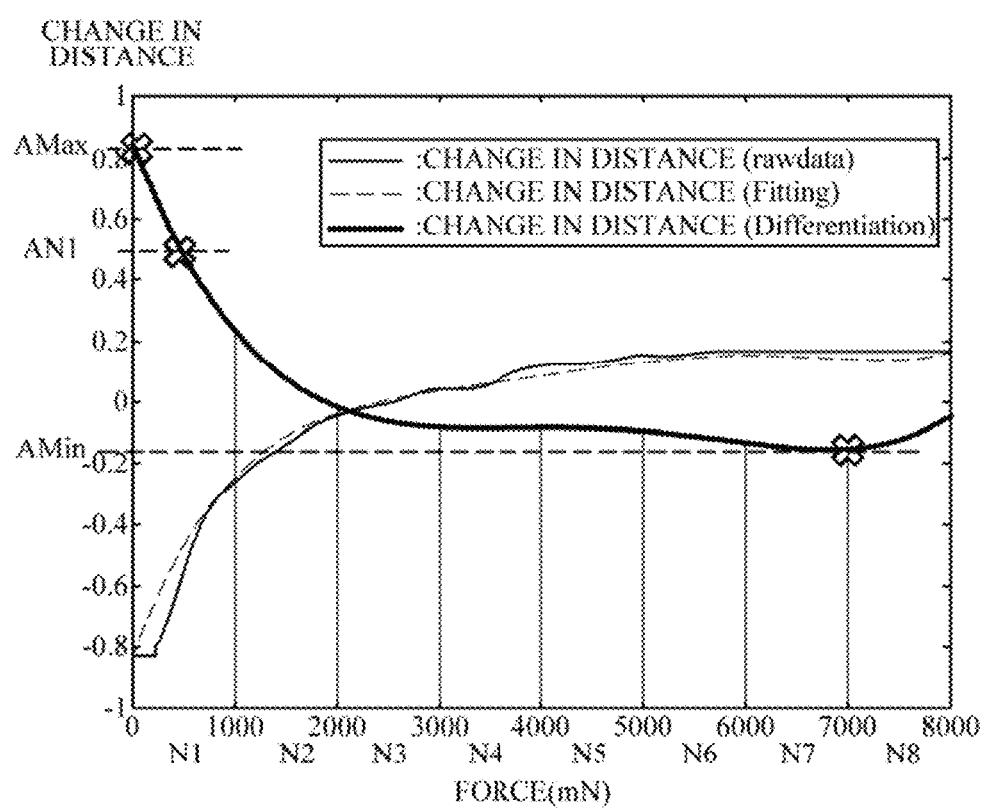

Referring to FIG. 6B, based on the differential graph, the second feature value obtainer 320 may obtain, as the second feature value, a slope value AMax at a point where the change in distance is maximum, and/or a slope value Amin at a point where the change in distance is minimum. Further, the second feature value obtainer 320 may divide an axis of force/pressure into pre-defined unit intervals, and may obtain an average slope value of each unit interval as the second feature value. FIG. 6B illustrates eight unit intervals N1, N2, N3, N4, N5, N6, N7, and N8 divided in units of 1000 mN. For example, the second feature value obtainer 320 may obtain, as an average slope value AN1, an average value (about 0.5) between a differential value (about 0.8) at a start point (point where a force/pressure value is 0) of the first unit interval N1 and a differential value (about 0.2) at an end point (point where a force/pressure value is 1000) of the first unit interval N1. In this manner, the second feature value obtainer 320 may obtain an average slope value of each of the eight unit intervals N1, N2, N3, N4, N5, N6, N7, and N8.

Referring back to FIG. 3A, the estimator 340 may estimate bio-information by combining the obtained first, second, and third feature values. In this case, the estimator 340 may estimate bio-information by applying a pre-defined bio-information estimation model to the values as represented by the following Equation 1. The bio-information estimation model may be expressed in the form of various linear or non-linear combination functions, such as addition, subtraction, division, multiplication, logarithmic value, regression equation, and the like, with no particular limitation. For example, the following Equation 1 represents a simple linear function.

$$y = af_1 + bf_2 + cf_3 + d \qquad \text{[Equation 1]}$$

Herein, y denotes bio-information to be obtained, e.g., diastolic blood pressure, systolic blood pressure, mean arterial pressure, etc.; $f_1$ denotes the first feature value, $f_2$ denotes the second feature value, and $f_3$ denotes the third feature value. Further, a, b, c, and d denote coefficients for weighting each of the feature values, and may be a fixed value which may be applied generally to a plurality of users pre-defined according to types of bio-information, or may be adjusted for each user according to user characteristic and the like. Herein, $f_1$ may be any one, or a combination of two or more, of the first feature values; $f_2$ may be any one, or a combination of two or more, of the second feature values; and $f_3$ may be any one, or a combination of two or more, of the third feature values. In this case, criteria for combining the feature values may be defined differently according to types of bio-information to be obtained, and may be defined properly for each user according to user characteristics.

Figure 3B:
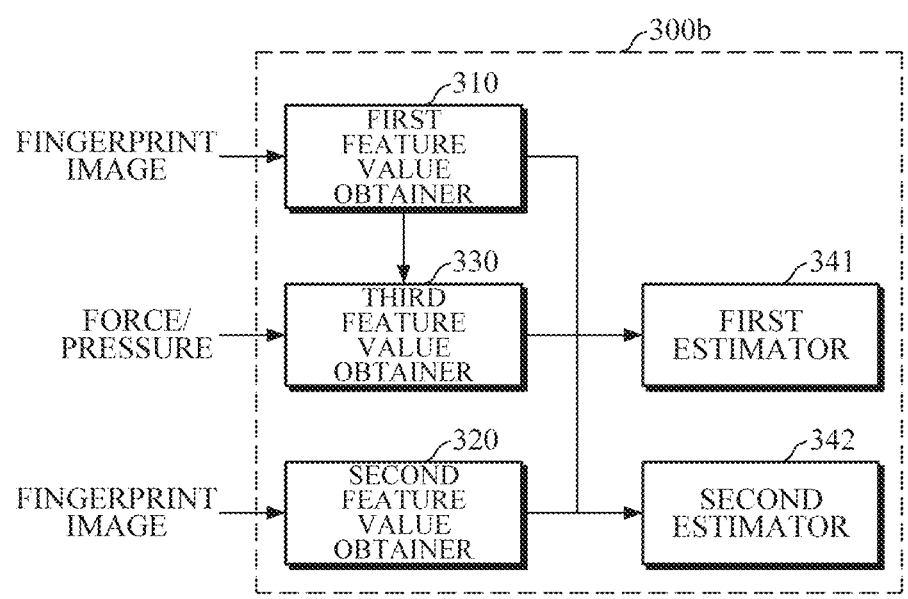

FIG. 3B is a diagram illustrating another example of a configuration of a processor of an apparatus for estimating bio-information.

Referring to FIG. 3B, a processor 300b according to an embodiment includes the first feature value obtainer 310, the second feature value obtainer 320, the third feature value obtainer 330, a first estimator 341, and a second estimator 342. The first feature value obtainer 310, the second feature value obtainer 320, the third feature value obtainer 330 are described above with reference to FIG. 3A.

The first estimator 341 may estimate first bio-information by using any one, or a combination of two or more of, the first feature value, the second feature value, and the third feature value. In this case, the first bio-information may be blood pressure.

Figure 6C:
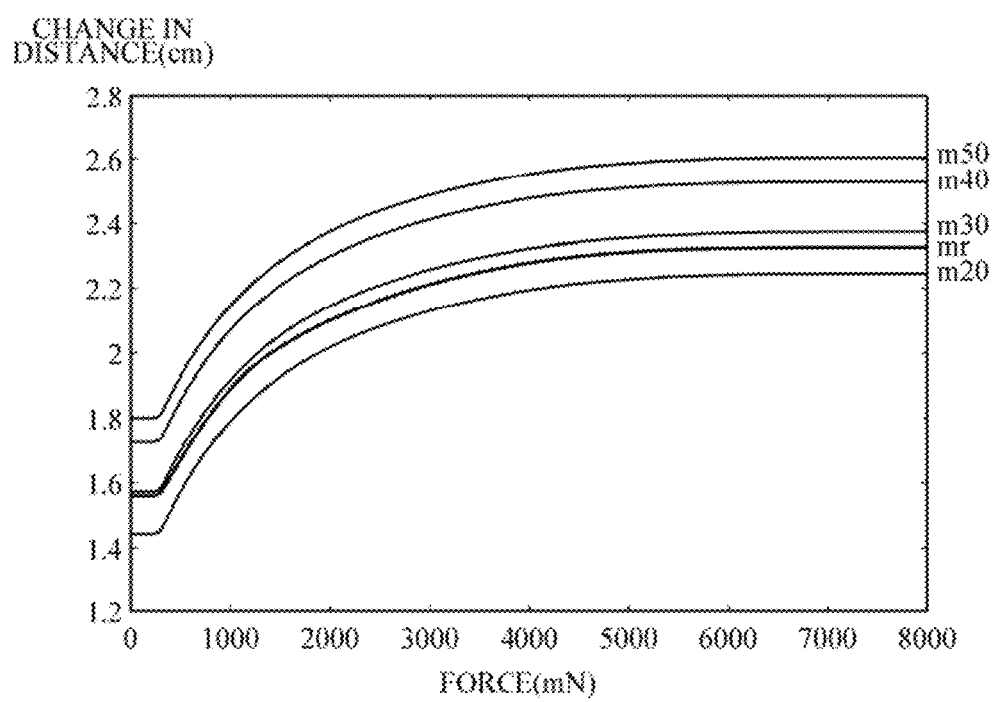

The second estimator 342 may estimate second bio-information based on the second feature value. In this case, the second bio-information may be skin elasticity and/or skin age. For example, FIG. 6C illustrates a change in distance between valleys or ridges for each age group when a force is equally changed by the finger. For example, an overall mean change mr of a plurality of subjects, a mean change m20 of subjects in their 20s, a mean change m30 of subjects in their 30s, a mean change m40 of subjects in their 40s, and a mean change m50 of subjects in their 50s. As illustrated in FIG. 6C, as the age increases, there is a greater change in distance for the equal contact force. The result generally shows that as the age increases, skin elasticity decreases and skin age increases.

The second estimator 342 may estimate skin elasticity and/or skin age for each user by considering general skin characteristics. For example, the second estimator 342 may estimate the skin elasticity and/or skin age by considering a trend of a change in second feature obtained from a specific user, compared to a reference second feature value obtained at a reference time. The following description is given of some examples thereof, but the present disclosure is not limited thereto.

For example, the second estimator 342 may estimate the skin elasticity and/or skin age by applying a pre-defined estimation model to a trend of the change in second feature value obtained from a specific user, compared to the reference second feature value obtained based on a mean change of a plurality of subjects. In this case, the estimation model may be defined as various linear or non-linear combination functions using a difference between the reference second feature value and the second feature value, obtained from the user, as an input. However, the estimation model is not limited thereto.

In another example, the reference second feature value may be obtained for each age group, gender, occupation, and health condition, or may be divided into various groups based on a combination thereof. Based on obtaining the second feature value for a specific user, the second estimator 342 may compare the second feature value obtained for the user with a reference second feature value for each group, and may estimate skin elasticity and/or skin age of the user by using skin elasticity and/or skin age of a corresponding group.

In another example, the second estimator 342 may relatively estimate that as a change in the second feature value obtained at a current time shows an increasing/decreasing trend, compared to the reference second feature value obtained from a specific user at a reference time, the skin elasticity decreases/increases, and the skin age increases/decreases.

In addition, the processor 300b in the embodiment of FIG. 3B may include a mode controller. The mode controller may operate in a mode for estimating first bio-information, a mode for estimating second bio-information, and a mode for estimating both the first and second bio-information.

For example, if the mode for estimating the first bio-information is set as a basic mode, or in response to a user's request for estimating the first bio-information, the mode controller may estimate the first bio-information by driving the first feature value obtainer 310, the second feature value obtainer 320, the third feature value obtainer 330, and the first estimator 341. In another example, if the mode for estimating the second bio-information is set as a basic mode, or in response to a user's request for estimating the second bio-information, the mode controller may estimate the second bio-information by driving the second feature value obtainer 320 and the second estimator 342. In yet another example, if the mode for estimating both the first and second bio-information is set as a basic mode, or in response to a user's request for estimating both the first and second bio-information, the mode controller may estimate both the first and second bio-information by driving the first feature value obtainer 310, the second feature value obtainer 320, the third feature value obtainer 330, the first estimator 341, and the second estimator 342.

Figure 7:
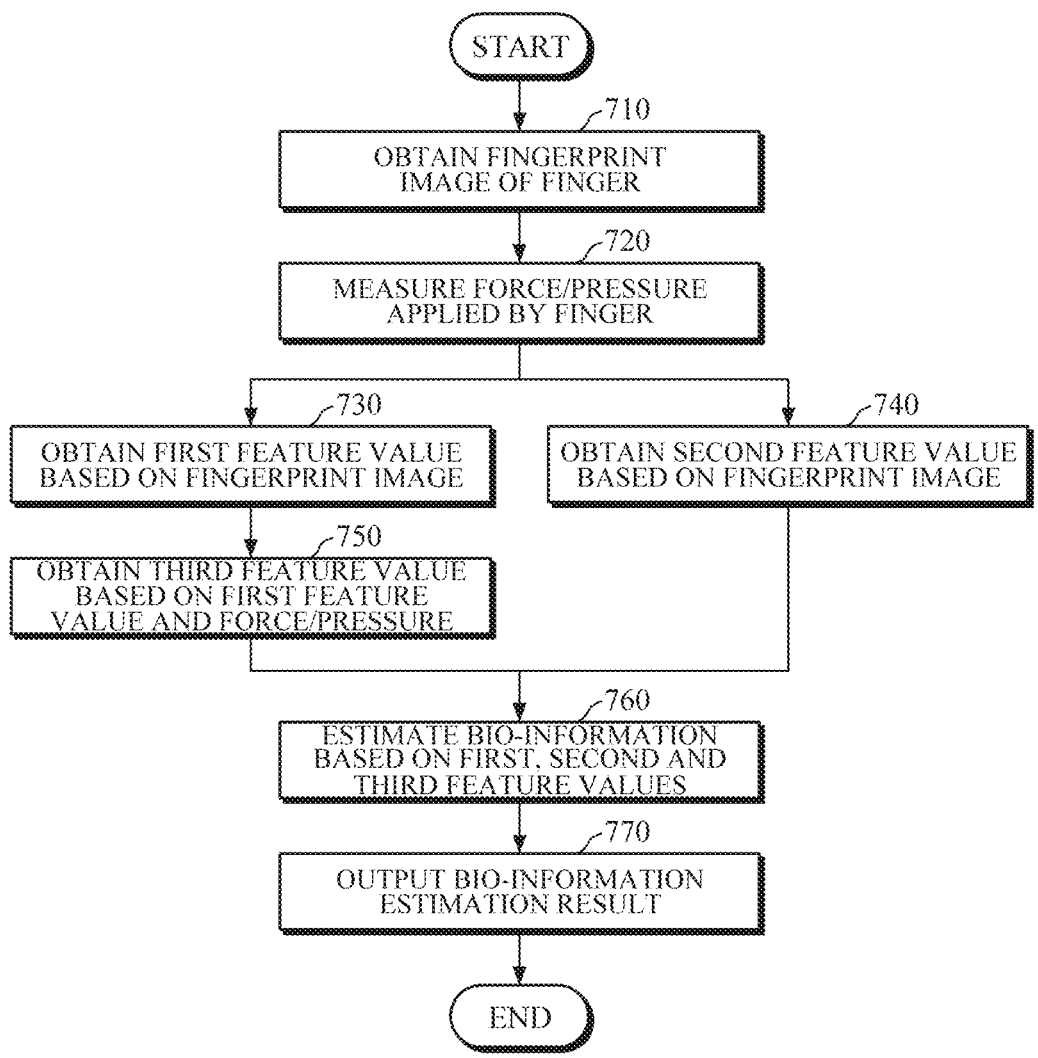
FIG. 7 is a flowchart illustrating a method of estimating bio-information according to an embodiment of the present disclosure.

FIG. 7 is a flowchart illustrating a method of estimating bio-information according to an embodiment of the present disclosure. The method of FIG. 7 is an example of a method of estimating bio-information which is performed by the apparatuses 100 and 200 for estimating bio-information of FIGS. 1 and 2, which are described above in detail, and thus will be briefly described below.

In response to a request for estimating bio-information, the apparatuses 100 and 200 for estimating bio-information may obtain a fingerprint image of a finger in operation 710. The request for estimating bio-information may be received at predetermined intervals or from a user or an external device. In this case, based on receiving the request for estimating bio-information, the apparatuses 100 and 200 for estimating bio-information may guide force or pressure to be applied by a user's finger to the sensor part.

Then, the apparatuses 100 and 200 for estimating bio-information may measure the force or pressure applied by the finger to the sensor part while the fingerprint image of the finger is obtained in operation 720. The user may change pressure between the finger and the sensor part by gradually increasing a pressing force when the user places the finger on the sensor part, or by gradually decreasing a pressing force when the user presses the sensor part with a force greater than or equal to a threshold value. Alternatively, when the finger is in contact with the sensor part, the finger may be pressed by an external force to change the pressure between the finger and the sensor part.

Subsequently, the apparatuses 100 and 200 for estimating bio-information may obtain a first feature value based on the fingerprint image in operation 730. For example, the apparatuses 100 and 200 for estimating bio-information may obtain a pulse wave signal based on a change in intensity of fingerprint images which are obtained continuously, and may obtain a maximum amplitude value of the pulse wave signal as the first feature value.

Next, the apparatuses 100 and 200 for estimating bio-information may obtain a second feature value based on the fingerprint image in operation 740. For example, the apparatuses 100 and 200 for estimating bio-information may obtain a distance between valleys or ridges of a fingerprint based on the fingerprint image, and may obtain a second feature value based on a change in the distances obtained during a predetermined period of time. For example, the second feature value may include a slope value at a point where a change in the distance is maximum, a slope value at a point where a change in the distance is minimum, and/or an average slope value obtained in each of unit intervals when an axis of force/pressure is divided into predetermined unit intervals in a graph of a fingerprint pattern change, which shows a change in the distance vs. force/pressure. In this case, operations 730 and 740 are not necessarily performed in time sequence, but may be performed at the same time.

Then, the apparatuses 100 and 200 for estimating bio-information may obtain a third feature value in 750 based on the first feature value obtained in 730 and the force/pressure obtained in 720. For example, the apparatuses 100 and 200 for estimating bio-information may obtain, as the third feature value, a force/pressure value at a point in time corresponding to the first feature value.

Subsequently, the apparatuses 100 and 200 for estimating bio-information may estimate bio-information by combining the first, second and third feature values in operation 760. For example, the apparatuses 100 and 200 for estimating bio-information may estimate bio-information, e.g., blood pressure, by applying a pre-defined weight to each of the first, second and third feature values, and by linearly or nonlinearly combining the weighted values.

Next, the apparatuses 100 and 200 for estimating bio-information may output a bio-information estimation result in operation 770. In this case, the apparatuses 100 and 200 for estimating bio-information may output the bio-information estimation result by properly using a display module, a speaker module, a haptic module by vibrations, tactile sensation, etc., and the like.

Figure 8:
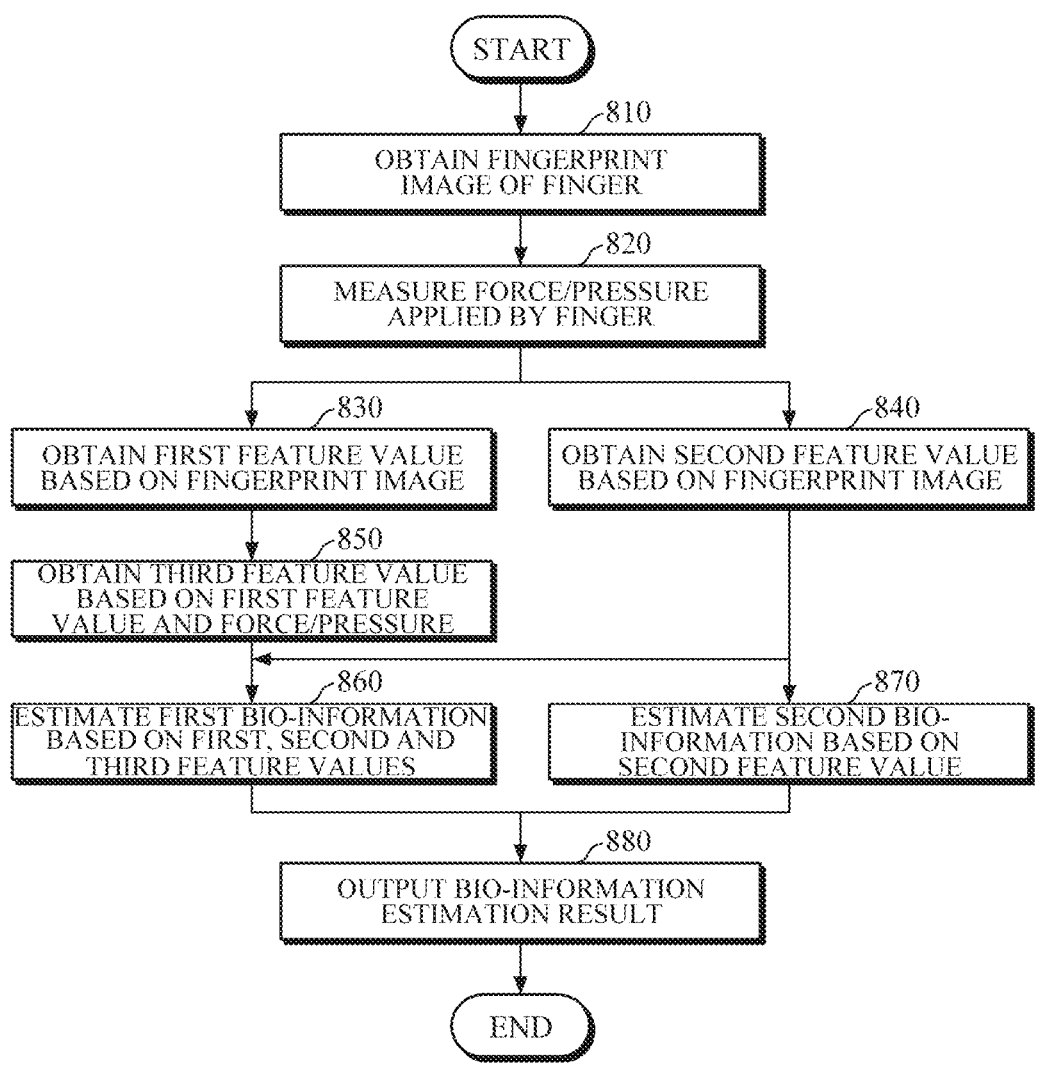
FIG. 8 is a flowchart illustrating a method of estimating bio-information according to another embodiment of the present disclosure.

FIG. 8 is a flowchart illustrating a method of estimating bio-information according to another embodiment of the present disclosure. The method of FIG. 8 is an example of a method of estimating bio-information which is performed by the apparatuses 100 and 200 for measuring bio-information of FIGS. 1 and 2, which will be briefly described below.

In response to a request for estimating bio-information, the apparatuses 100 and 200 for estimating bio-information may obtain a fingerprint image of a finger in operation 810.

Then, the apparatuses 100 and 200 for estimating bio-information may measure force or pressure applied by the finger to the sensor part while the fingerprint image of the finger is obtained in operation 820.

Subsequently, based on the fingerprint image, the apparatuses 100 and 200 for estimating bio-information may obtain a first feature value in operation 830 and a second feature value in operation 840, and may obtain a third feature value in operation 850 based on the first feature value obtained in operation 830 and the force/pressure obtained in operation 820.

Next, the apparatuses 100 and 200 for estimating bio-information may estimate first bio-information by combining the first, second, and third feature values in operation 860, and may estimate second bio-information in operation 870 based on the second feature value obtained in 840. In this case, the first bio-information may be blood pressure, and the second information may be skin elasticity and/or skin age.

Then, the apparatuses 100 and 200 for estimating bio-information may output a bio-information estimation result in operation 880.

Figure 9:
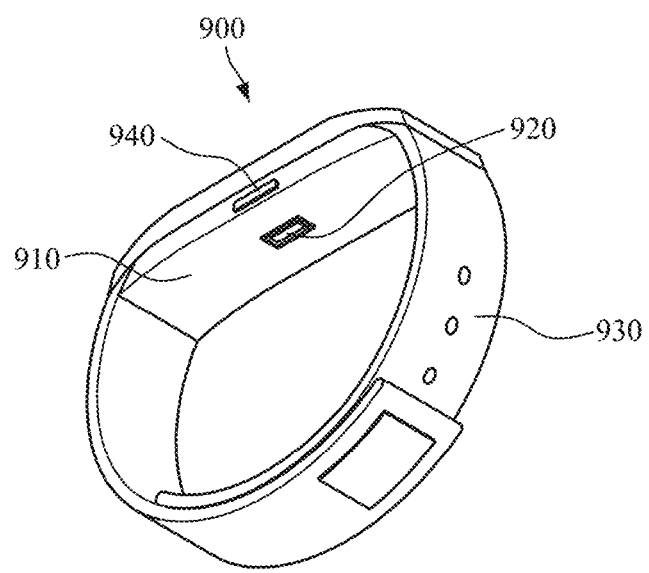
FIG. 9 is a diagram illustrating a wearable device according to an embodiment of the present disclosure.

FIG. 9 is a diagram illustrating an example of a wearable device, to which the embodiments of the apparatuses 100 and 200 for estimating bio-information are applied. As illustrated in FIG. 9, the wearable device may be a smart watch worn on a wrist or a smart band type wearable device, but is not limited thereto, and examples thereof may include a smart ring, a smart necklace, smart glasses, and the like.

Referring to FIG. 9, the wearable device 900 includes a main body 910 and a strap 930.

The strap 930, which is connected to both ends of the main body 910, may be flexible so as to be bent around a user's wrist. The strap 930 may be composed of a first strap and a second strap which are separated from each other. Respective ends of the first strap and the second strap are connected to the main body 910, and the other ends thereof may be connected to each other via a connecting means. In this case, the connecting means may be formed as magnetic connection, Velcro connection, pin connection, and the like, but is not limited thereto. Further, the strap 930 is not limited thereto, and may be integrally formed as a non-detachable band.

In this case, air may be injected into the strap 930, or the strap 930 may be provided with an air bladder, so that the strap 930 may have elasticity according to a change in pressure applied to the wrist, and may transmit the change in pressure of the wrist to the main body 910.

A battery may be embedded in the main body 910 or the strap 930 to supply power to the wearable device 900.

Furthermore, the main body 910 may include a sensor part 920 mounted on one side thereof. The sensor part 920 may include a first sensor for obtaining a fingerprint image of a finger, and a second sensor for measuring force/pressure applied by the finger to the first sensor. The first sensor may include a light source and a CMOS image sensor (CIS). In addition, the second sensor may include a force sensor, a pressure sensor, an area sensor, and the like.

A processor may be mounted in the main body 910. The processor may estimate bio-information based on the obtained fingerprint image of the finger and the obtained force/pressure. For example, the processor may obtain a first feature value, related to pulse waves, based on the fingerprint image of the finger, may obtain the second feature value related to skin elasticity, and may obtain a third feature value based on the force/pressure. In addition, by combining the first, second, and third feature values, the processor may estimate bio-information, such as blood pressure, skin elasticity, skin age, and the like.

Based on receiving a request for estimating bio-information from a user, the processor may guide a user on force/pressure through a display, and based on estimating bio-information, the processor may provide a bio-information estimation result for the user through the display. The display may be mounted on a front surface of the main body 910, may output the guide information and/or the bio-information estimation result, and may receive a user's touch input and transmit the touch input to the processor.

Further, the main body 910 may include a storage which stores information processed by the processor, reference information for estimating bio-information, and the like.

In addition, the main body 910 may include a manipulator 940 which receives a user's control command and transmits the received control command to the processor. The manipulator 940 may be mounted on a side surface of the main body 910, and may have a function to input a command to turn on/off the wearable device 900.

Moreover, the wearable device 900 may include a communication interface provided for transmitting and receive various data with an external device, and various other modules for additional functions provided by the wearable device 900/

Figure 10:
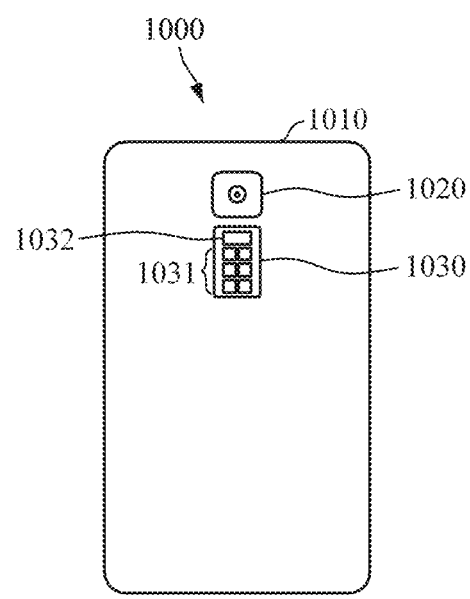
FIG. 10 is a diagram illustrating an example of a smart device, to which an apparatus for estimating bio-information is applied.

FIG. 10 is a diagram illustrating an example of a smart device, to which the embodiments of the apparatuses 100 and 200 for estimating bio-information are applied. In this case, the smart device may be a smartphone, a tablet PC, and the like.

Referring to FIG. 10, the smart device 1000 includes a main body 1010 and a sensor part 1030 mounted on one surface of the main body 1010. The sensor part 1030 may include a first sensor including one or more light sources 1031 and a detector 1032, and a second sensor disposed at a lower end of the first sensor and measuring force/pressure applied by a finger to the first sensor. In this case, the detector 1032 may include a CMOS image sensor (CIS) 1032.

As illustrated in FIG. 10, the main body 1010 may include an image sensor 1020. The image sensor 1020 captures various images, and may acquire a fingerprint image of a finger when the finger touches the sensor part 1030. If the CMOS image sensor 1032 is mounted in the first sensor of the sensor part 1030, the image sensor 1020 may be omitted.

A processor may be mounted in the main body 1010, and may estimate bio-information, such as blood pressure, skin elasticity or skin age, based on the fingerprint image of the finger and the force/pressure, which are obtained by the sensor part 1030.

Furthermore, a display, a communication interface, etc., may be mounted in the main body 1010, to output and provide bio-information processed by the processor to a user or to transmit the bio-information to an external device. Various other modules for performing various functions may be mounted in the main body 1010.

The embodiments of the present disclosure can be implemented by computer-readable code written on a non-transitory computer-readable medium and executed by a processor. The non-transitory computer-readable medium may be any type of recording device in which data is stored in a computer-readable manner.

Examples of the non-transitory computer-readable medium include a ROM, a RAM, a CD-ROM, a magnetic tape, a floppy disc, an optical data storage, and a carrier wave (e.g., data transmission through the Internet). The non-transitory computer-readable medium can be distributed over a plurality of computer systems connected to a network so that a computer-readable code is written thereto and executed therefrom in a decentralized manner. Functional programs, code, and code segments for implementing the embodiments of the present disclosure can be deduced by programmers of ordinary skill in the art to which the present disclosure pertains.

The present disclosure has been described herein with regard to example embodiments. However, it will be obvious to those skilled in the art that various changes and modifications can be made without changing technical conception and features of the present disclosure. Thus, it is clear that the above-described embodiments are illustrative in all aspects and are not intended to limit the present disclosure.

What is claimed is:

1. An apparatus for estimating bio-information of a user, the apparatus comprising:
    a first sensor configured to obtain a fingerprint image of a finger of the user, wherein the first sensor comprises:
        one or more light sources configured to emit light onto the finger; and one or more complementary metal-oxide semiconductor (CMOS) image sensors;
    a second sensor configured to measure a force or a pressure applied by the finger; and
    a processor configured to:
        obtain, based on the fingerprint image, a first feature value related to pulse waves and a second feature value related to skin elasticity;
        obtain a third feature value based on the force or the pressure; and
        estimate the bio-information of the user based on the first feature value, the second feature value, and the third feature value.

2. The apparatus of claim 1, wherein the processor is further configured to:
    obtain a pulse wave signal based on the fingerprint image; and
    obtain the first feature value based on at least one of a maximum amplitude value and a minimum amplitude value of the pulse wave signal.

3. The apparatus of claim 1, wherein the processor is further configured to:
    obtain a change in distance between ridges or valleys of a fingerprint from the fingerprint image based on the finger pressing the first sensor; and
    obtain the second feature value based on the change in distance.

4. The apparatus of claim 3, wherein the processor is further configured to:
    obtain a first average of distances between the ridges or the valleys at one or more points of first fingerprint images obtained continuously over a predetermined period of time, and a second average of the distances at one or more points of a second fingerprint image; and
    obtain a difference between the first average and the second average as the change in distance.

5. The apparatus of claim 3, wherein the processor is further configured to:
    generate a graph of a fingerprint pattern change based on the change in distance; and
    obtain the second feature value based on the graph of the fingerprint pattern change.

6. The apparatus of claim 5, wherein the processor is further configured to:
    obtain, as the second feature value, at least one of a maximum slope value, a minimum slope value, and an average slope value of each of pre-defined unit intervals.

7. The apparatus of claim 6, wherein the processor is further configured to:
    generate a differential graph by differentiating the graph of the fingerprint pattern change; and
    obtain the second feature value by using the differential graph.

8. The apparatus of claim 1, wherein the processor is further configured to:
    obtain a force value or a pressure value at a point in time, corresponding to the first feature value, as the third feature value.

9. The apparatus of claim 1, wherein the processor is further configured to:
    combine the first feature value, the second feature value, and third feature value; and
    estimate the bio-information by applying a pre-defined estimation model to a result of combining the first feature value, the second feature value, and the third feature value.

10. The apparatus of claim 9, wherein the processor is further configured to:
apply a first weight to the first feature value to obtain a first weighted value;
apply a second weight to the second feature value to obtain a second weighted value;
apply a third weight to the third feature value to obtain a third weighted value; and combine the first weighted value, the second weighted value, and the third weighted value.

11. The apparatus of claim 10, wherein each of the first weight value, the second weight value, and the third weight value is a pre-defined fixed value, or is a value adjusted by considering at least either user characteristics or types of bio-information.

12. The apparatus of claim 1, wherein the processor is further configured to:
while the fingerprint image is obtained from the finger, control an output interface to output guide information to guide a user regarding pressure between the finger and the first sensor.

13. The apparatus of claim 1, wherein the bio-information comprises one or more of blood pressure, vascular age, arterial stiffness, aortic pressure waveform, vascular compliance, stress index, and fatigue level.

14. A method of estimating bio-information of a user, the method comprising:
obtaining a fingerprint image of a finger of the user by a sensor, wherein the sensor comprises: one or more light sources configured to emit light onto the finger; and one or more complementary metal-oxide semiconductor (CMOS) image sensors;
measuring a force or a pressure applied by the finger;
obtaining a first feature value related to pulse waves based on the fingerprint image;
obtaining a second feature value related to skin elasticity based on the fingerprint image;
obtaining a third feature value based on the force or the pressure; and
estimating the bio-information based on the first feature value, the second feature value, and the third feature value.

15. The method of claim 14, wherein the obtaining of the first feature value comprises:
obtaining a pulse wave signal from the fingerprint image; and
obtaining the first feature value based on at least one of a maximum amplitude value and a minimum amplitude value of the pulse wave signal.

16. The method of claim 15, wherein the obtaining of the second feature value comprises:
obtaining a change in distance between ridges or valleys of a fingerprint from the fingerprint image based on the finger pressing the sensor; and
obtaining the second feature value based on the obtained change in distance.

17. The method of claim 16, wherein the obtaining of the second feature value comprises:
obtaining a first average of first distances between the ridges or the valleys at one or more points of first fingerprint images obtained continuously over a predetermined period of time;
obtaining a second average of second distances between the ridges or the valleys at one or more points of a second fingerprint image; and
obtaining a difference between the first average and the second average as the change in distance.

18. The method of claim 16, wherein the obtaining of the second feature value comprises:
generating a graph of a fingerprint pattern change based on the change in distance; and
obtaining the second feature value based on the graph of the fingerprint pattern change.

19. The method of claim 18, wherein the obtaining of the second feature value comprises obtaining, as the second feature value, at least one of a maximum slope value, a minimum slope value, and an average slope value of each of pre-defined unit intervals.

20. The method of claim 14, wherein the obtaining of the third feature value comprises obtaining a force value or a pressure value at a point in time, corresponding to the first feature value, as the third feature value.

21. The method of claim 14, wherein the estimating of the bio-information comprises combining the first feature value, the second feature value, and the third feature value; and
estimating the bio-information by applying a pre-defined estimation model to a result of combining the first feature value, the second feature value, and the third feature value.

22. The method of claim 15, further comprising:
while the fingerprint image is being obtained from the finger, guiding a user regarding pressure between the finger and the sensor.

23. An apparatus for estimating bio-information of a user, the apparatus comprising:
a first sensor configured to obtain a fingerprint image of a finger of the user, wherein the first sensor comprises: one or more light sources configured to emit light onto the finger; and one or more complementary metal-oxide semiconductor (CMOS) image sensors;
a second sensor configured to measure a force or a pressure applied by the finger; and
a processor configured to:
obtain two or more feature values based on at least one of the fingerprint image and the force or the pressure; and
estimate first bio-information and second bio-information, based on the two or more feature values.

24. The apparatus of claim 23, wherein:
the first bio-information comprises blood pressure; and
the processor is further configured to:
obtain a first feature value and a second feature value based on the fingerprint image;
obtain a third feature value based on the first feature value and the force or the pressure; and
estimate the blood pressure by combining the first feature value and the second feature value.

25. The apparatus of claim 23, wherein:
the second bio-information comprises at least one of skin elasticity and skin age; and
the processor is further configured to:
obtain the second feature value based on the fingerprint image; and
estimate at least one of the skin elasticity and the skin age based on the second feature value.

26. The apparatus of claim 25, wherein the processor is further configured to:
obtain a change in distance between ridges or valleys of the fingerprint from the fingerprint image based on the finger pressing the first sensor; and
obtain the second feature value based on the change in distance.

27. The apparatus of claim 25, wherein the processor is further configured to:
estimate that the skin elasticity decreases or increases, and that the skin age increases or decreases as a change in the second feature value shows an increasing or decreasing trend, compared to a second feature value obtained at a reference time.

28. An apparatus for estimating bio-information of a user, the apparatus comprising:
- a sensor configured to obtain a fingerprint image of a finger of the user based on the finger pressing the sensor, wherein the sensor comprises: one or more light sources configured to emit light onto the finger; and one or more complementary metal-oxide semiconductor (CMOS) image sensors; and
- a processor configured to:
  - obtain feature values from the fingerprint image based on a fingerprint pattern change based on the finger pressing the sensor; and
  - estimate at least one of skin elasticity and skin age based on the feature values.

29. The apparatus of claim 28, wherein:
the sensor is further configured to measure a force or a pressure applied by the finger; and
the processor is further configured to:
- obtain a change in distance between ridges or valleys of the fingerprint from the fingerprint image based on the finger pressing the sensor;
- generate a graph of a fingerprint pattern change by plotting the change in distance against the force or the pressure; and
- obtain the feature values by using the graph of the fingerprint pattern change.

* * * * *